United States Patent [19]

Fahmy

[11] 4,450,158
[45] May 22, 1984

[54] S-TERTIARY ALKYL PHOSPHOROAMIDODITHIOATE PESTICIDES

[75] Inventor: Mohamed A. H. Fahmy, Princeton, N.J.

[73] Assignee: FMC Corporation, Philadelphia, Pa.

[21] Appl. No.: 377,651

[22] Filed: May 13, 1982

[51] Int. Cl.³ .................... A01N 57/28; C07F 9/44
[52] U.S. Cl. ................................. 424/220; 260/959
[58] Field of Search ..................... 424/220; 260/959

[56] References Cited

U.S. PATENT DOCUMENTS 3,641,222  2/1972  Botts et al. ................ 260/959
4,258,038  3/1981  Strong ...................... 260/961

FOREIGN PATENT DOCUMENTS 1402296  8/1975  United Kingdom ............ 260/959

341802  8/1972  U.S.S.R. ..................... 260/959

Primary Examiner—Anton H. Sutto
Attorney, Agent, or Firm—Robert L. Andersen; H. Robinson Ertelt

[57] ABSTRACT

Compounds of the formula

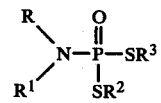

in which R and $R^1$ are alkyl of 1 to 4 carbon atoms, $R^2$ is a tertiary alkyl group of 4 to 8 carbon atoms, and $R^3$ is an alkyl group of 1 to 8 carbon atoms, insecticidal and nematicidal compositions thereof, and a method for controlling such pests are disclosed.

6 Claims, No Drawings

S-TERTIARY ALKYL PHOSPHOROAMIDODITHIOATE PESTICIDES

The present invention relates to a new class of compounds for control of insects and nematodes, namely tertiary alkyl phosphoroamidodithioates, to insecticidal/nematicidal compositions thereof, and to a method for control of nematodes and soil-borne insects.

U.K. Pat. No. 1,402,296 discloses a genus of phosphoramidodithioates in which the sulfur atoms are each substituted with ethyl, propyl or isopropyl. These compounds are said to be useful as fungicides for rice, but are not reported to have any nematicidal or insecticidal activity.

U.S. Pat. No. 3,641,222 discloses S,S-dialkyl-amidodithiophosphates having defoliant, desiccant, insecticidal, and acaricidal properties. The disclosure is limited to compounds in which the two alkyl groups appended to sulfur have 1 to 4 carbon atoms and are identical.

The compounds of this invention are S-tertiary alkyl phosphoroamidodithioates of the formula:

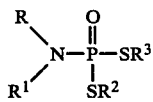

in which R and $R^1$ are alkyl groups of 1, 2, 3, or 4 carbon atoms, $R^2$ is a tertiary alkyl group of 4 to 8 carbon atoms, preferably 4 to 6 carbon atoms, and $R^3$ differs from $R^2$ and is an alkyl group of 1 to 6 carbon atoms, preferably 2 to 4 carbon atoms, straight or branched chain, or a cyclic alkyl group of 5 or 6 carbon atoms. In one embodiment the invention comprises a compound of formula I in which $R^2$ is tert-butyl; in another, a compound in which $R^2$ is tert-pentyl. In either or both of these embodiments R and $R^1$ may be the same or different, and $R^3$ may advantageously be ethyl, propyl, butyl, isobutyl or sec-butyl.

With reference to formula I, the following compounds may be specifically mentioned:

| Compound No. | R | $R^1$ | $R^2$ | $R^3$ |
|---|---|---|---|---|
| 1 | methyl | methyl | tert-butyl | ethyl |
| 2 | " | " | " | propyl |
| 3 | " | " | " | butyl |
| 4 | " | " | " | isobutyl |
| 5 | " | " | tert-pentyl | ethyl |
| 6 | methyl | methyl | tert-pentyl | propyl |
| 7 | " | " | " | butyl |
| 8 | " | " | " | isobutyl |
| 9 | " | " | " | sec-butyl |
| 10 | " | " | tert-butyl | sec-butyl |
| 11 | ethyl | ethyl | tert-butyl | propyl |

The following example illustrates preparation of the compounds of this invention.

EXAMPLE 1

Synthesis of S-propyl S-tert-pentyl N,N-dimethylphosphoroamidodithioate

Step A: Synthesis of S-propyl phosphorothioic dichloride. To a solution of 76.0 g (1.0 mole) of 1-propanethiol in 300 ml of toluene was added dropwise 148.0 g (1.1 mole) of sulfuryl chloride while maintaining the temperature of the reaction mixture at −3° to 7° C. Upon completion of addition, 60.05 g (1.0 mole) of acetic acid was added in one portion. After 137.3 g (1.0 mole) of phosphorus trichloride was added dropwise the reaction mixture was allowed to warm to 12° C. at which temperature it was stirred for 1.5 hours. The temperature was then allowed to reach ambient conditions and stirring was continued for approximately 90 hours. An additional 5.4 g (0.037 mole) of sulfuryl chloride was added and the mixture stirred for 20 minutes until hydrogen chloride evolution ceased. The solvent was evaporated under a vacuum, and the liquid residue was distilled. The product, S-propyl phosphorothioic dichloride, was isolated as a single fraction weighing 146.75 g/b.p. 64° C./0.6 mm of Hg.

Step B: Synthesis of S-propyl N,N-dimethylphosphoroamidothioic chloride. Under a nitrogen atmosphere to a solution of 52.8 g (0.27 mole) of S-propyl phosphorothioic dichloride (Step A product) in 250 ml of toluene cooled to 0° C. was added dropwise 27.4 g (0.27 mole) of triethylamine. While maintaining the temperature of the reaction mixture between 0° C. and 10° C., a solution of 14.9 g (0.33 mole) of dimethylamine in 150 ml of toluene was added dropwise. The temperature was allowed to rise to ambient conditions, and the mixture was stirred overnight. After filtering off the solid salt, the solvent was evaporated under vacuum from the filtrate, leaving an orange oil (57.7 g) as a residue. The oil was distilled, yielding 45.3 g of S-propyl N,N-dimethylphosphoroamidothioic chloride, b.p. 74°–78° C./0.03 mm of Hg. Both proton and phosphorus nmr spectra were consistent with the assigned structure.

Step C: Synthesis of S-propyl S-tert-pentyl N,N-dimethylphosphorodithioate. To a suspension of 0.9 g (0.035 mole) of sodium hydride in 50 ml of tetrahydrofuran under a nitrogen atmosphere was added dropwise 3.7 g (0.035 mole) of 2-methyl-2-butanethiol. The reaction mixture was warmed to 50° C. and then cooled to ambient conditions after hydrogen evolution had ceased. To this mixture was added 7.1 g (0.035 mole) of S-propyl N,N-dimethylphosphoroamidothioic chloride in one portion. The reaction mixture was stirred for approximately 64 hours before the solvent was evaporated under vacuum. The residue was dissolved in 50 ml of toluene. This solution was washed three times with 25 ml of water, dried over anhydrous sodium sulfate, filtered, and the solvent was evaporated under vacuum, leaving 8.77 g of an oil. This oil was distilled under vacuum, yielding the following three fractions:

1. 0.3 g, b.p. 70°–80° C./0.01 mm of Hg
2. 1.63 g, b.p. 94°–104° C./0.01 mm of Hg
3. 5.2 g, b.p. 105°–111° C./0.01 mm of Hg

Fraction 3 was shown to be S-propyl S-tert-pentyl N,N-dimethylphosphoroamidodithioate by proton and phosphorus nmr analyses.

The compounds of this invention are useful for control plant pests, particularly nematodes and soil-borne insects such as corn rootworm, wireworm, and cutworms. These compounds are highly effective against these plant pests on agricultural crops and have little or no phytotoxicity to the host plant. The compound is advantageously applied to or incorporated into the soil in which crops are planted or are to be planted, or are applied to the plant's roots.

The compounds are generally not applied full strength but are typically applied as formulations which may be applied as such or further diluted for application. Typical formulations include compositions of the active ingredient in combination with one or more agriculturally acceptable adjuvants, carriers or extenders, preferably with a surface active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application.

With due consideration to these factors the active ingredient of a typical formulation may, for example, be suitably present at a concentration of about 0.01% up to about 95%, preferably 0.1% up to 90%, of the formulation, agriculturally acceptable carriers, diluents, adjuvants, and other suitable active ingredients comprising the balance of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A suitable concentration of the active ingredient in the use dilution may be in the range of 0.005% to 10%, more preferably 0.01% to about 10%, by weight.

Many variations of spraying, dusting, and controlled or slow release compositions of a type known in the art may be used by substituting or adding an insecticidal compound or compounds of this invention into the compositions known or apparent to the art.

The insecticidal compounds of this invention may be formulated and applied with other compatible active agents including nematicides, insecticides, acaracides, fungicides, plant regulators, herbicides, fertilizers, and the like.

In applying these compounds, whether alone or with other agricultural chemicals, an effective insecticidal, acaricidal or nematicidal amount of the active ingredient must be applied. While the application rate will vary widely depending on the choice of compound, formulation, mode of application, plant species being protected, planting density, and other like factors, a suitable use rate for agricultural crops may be in the range of 0.005 to 3 kg/ha, preferably 0.01 to about 1 kg/ha.

The compounds of this invention were tested for insecticidal activity as described below.

Insect Topical Application and Filter Paper Tests

The test compound was dissolved in acetone and the resulting solution diluted with water to provide a test solution containing 500 nanograms/microliter. A 1 microliter droplet was applied to the second or third dorsal thoracic segment of each test larva. The insect was observed 24 hours later for toxic effect elicited by the test compound. An insect was considered dead if it could no longer right itself and move in an oriented pattern. The percent mortality for the test compounds against southern corn rootworm is reported in Table 1.

A filter paper test for corn rootworm control was carried out. Sufficient insecticide was dissolved in water to prepare test solutions containing varying concentrations of test chemical. A 100 mm diameter filter paper was placed in a disposable, plastic, 100 mm×15 mm petri dish and 2.5 ml of the test solution was poured onto the filter paper. After excess water had evaporated (1–1.5 hours), ten 3rd or 4th instar southern corn rootworm larvae were placed on the damp filter paper and the petri dish was covered. Two replicates of the test were carried out for each compound. Twenty-four hours after infestation the dead and moribund larvae were counted and the $LC_{50}$ (concentration in parts per million producing a 50 percent kill) was determined. The $LC_{50}$ is reported in Table 1.

Soil Incorporation Tests for Control of Southern Corn Rootworm

A solution of the test compound, containing 335 ppm test compound in 100 ml of a solution containing 90% water, 9.75% acetone and 0.25% octylphenoxypolyethoxyethanol, was stirred into topsoil in an amount sufficient to provide the desired concentration. The container for the test sample was capped and stored for the desired storage period (14 to 42 days). At the end of the storage period each test sample was infested with 10 larvae and a kernel of germinating corn as a food supply. The samples were then recapped and returned to storage for three days at which time the tests were read for percent mortality.

The soil samples varied from test to test. In some tests there was employed a "synthetic soil" containing 1 part topsoil, one and one-half parts sand; and one and one-half parts vermiculite. In other tests, various types of topsoil were employed. For purposes of the present tests no attempt was made to distinguish between soil types.

The initial and residual activity for some of the compounds of this invention were determined and are reported in Table I. The compounds tested showed excellent initial and residual activity against the Corn Rootworm.

Soil Incorporation Tests for Nematode Control and Phytotoxicity

Each compound was tested for nematicidal activity as a formulated material. The formulation used was a 5 wt. % dust formulation made up as follows:

| | |
|---|---|
| Active ingredient (100% active basis) | 5 parts |
| Base | 95 parts |
| 96% attaclay | |
| 2% highly purified sodium lignosulfonate (100%) | |
| 2% powdered sodium alkylnaphthalenesulfonate (75%) | |

The mixture was ground to a fine powder.

The formulation described above was tested for activity against root-knot nematode (*Meloidogyne incognita*) as follows:

Samples of infested soil were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue," Proc. Helm. Soc., Washington, 22, 87–89 (1955).] A 500 mesh sieve was used to collect the nematode larvae and eggs, and their number was estimated under a stereomicroscope.

Soil containing eggs and larvae was mixed with sufficient steam-sterilized sandy soil so that there were 800 to 1000 root-knot nematode larvae and eggs per pot of soil (three inch diameter each, containing approximately 300 g soil).

Soil so infested was used for soil incorporated nematicidal studies within two days of preparation. The formulated compounds to be tested for nematicidal activity were incorporated in the root-knot nematode infested potting soil to give soil treatment at several application rates in the range of 2.5 to 25 ppm (weight chemical/weight nematode infested soil). Young tomato plants were planted in this soil in three inch pots. At the end of two weeks the roots of all plants were examined and rated in comparison to untreated checks.

Control Treatments

The untreated check plants were treated in the same manner as those treated with the active ingredient.

The rating system and the results of the tests against root-knot nematode and phytotoxicity are shown in Table II. The results of the compounds in nematode tests varied widely, but the compounds uniformly showed low levels of phytotoxicity.

TABLE I

ACTIVITY AGAINST THE SOUTHERN CORN ROOTWORM[a]

| | | | Percent Mortality | | |
|---|---|---|---|---|---|
| | Filter | Topical | Initial | Residual Soil | |
| Compound | Paper Test $LC_{50}$ (ppm) | 500 ng/ insect | Soil 10 ppm | 14 days 10 ppm | 21 days | 42 days |
| 1 | 5.16 | 85 | 60 | | | |
| 2 | 1.67 | 70 | 100 | | | |
| 3 | 2.67 | 100 | | | | |
| 4 | 1.28 | 90 | | | | |
| 5 | 4.41 | 80 | 80 | | | |
| 6 | 2.62 | 100 | 100 | 100 | 95[d] | 100[c] |
| 7 | 2.64 | 65 | | | | |
| 8 | 1.21 | 35 | | | | |
| 9 | 2.34 | 70 | | | | |
| 10 | 2.31 | | | | | |
| 11 | 1.86 | | | | | |

[a]Diabrotica undecimpunctata howardi Barber
[b]Average of 2 results at 2.0 ppm
[c]at 2.00 ppm
[d]Average of 2 results at 1.00 ppm

TABLE II

ACTIVITY AGAINST THE ROOT-KNOT NEMATODE[a]

| | Root Knot Index[b] | | | | Plant Injury Rating[c] |
|---|---|---|---|---|---|
| Compound | 25 ppm | 10 ppm | 5 ppm | 2.5 ppm | |
| 1 | 4 | | | | 0 |
| 2 | 3 | | | | 1 |
| 3 | 3 | | | | 0 |
| 4 | 4 | | | | 0 |
| 5 | 0 | 1.4 | 2.5 | 3.5 | 1 |
| 6 | 0.33 | 0.9 | | | 1 |
| 7 | 1.5 | | | | 0 |
| 8 | 3.5 | | | | 0 |
| 9 | 0.95 | 3 | | | 1 |
| 10 | 2.75 | 4 | 4 | | 1 |

[a]Meloidogyne incognita
[b]Knot Index -
4 = no control
3 = 25% control
2 = 50% control
1 = 75% control
0.8 = 80% control
0.5 = 90% control
0.1-0.4 = 95-99% control
0 = complete control
[c]Plant Injury Rating -
0 = no injury
1 = slight phytotoxicity
2 = moderate phytotoxicity
3 = severe phytotoxicity
4 = plant not expected to survive

I claim:
1. An S-tertiary alkyl phosphoroamidodithioate of the formula

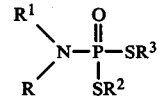

in which
R and $R^1$ are alkyl groups of 1 to 4 carbon atoms,
$R^2$ is a tertiary butyl or pentyl group, and $R^3$ differs from $R^2$ and is a straight or branched chain alkyl group of 1 to 6 carbon atoms or a cyclic alkyl group of 5 or 6 carbon atoms.

2. A method for controlling soil-borne insects and nematodes which comprises applying to plant roots or to the soil in which plants are planted or are to be planted an insecticidally and nematicidally effective amount of the compound of claim 1.

3. The compound of claim 1 in which $R^2$ is tert-butyl and $R^3$ is ethyl, propyl, butyl, or isobutyl.

4. The compound of claim 1 in which $R^2$ is tert-pentyl and $R^3$ is ethyl, propyl, butyl, isobutyl, or sec-butyl.

5. The compound of claim 1, 3, or 4, in which R and $R^1$ are methyl.

6. An insecticidal and nematicidal composition comprising an insecticidal and nematicidal amount of the compound of claim 1, 3, 4 or 5 in admixture with a compatible adjuvant diluent, or carrier.